(12) United States Patent
Gavriely

(10) Patent No.: US 7,513,256 B2
(45) Date of Patent: Apr. 7, 2009

(54) INTRA-AIRWAY VENTILATION

(76) Inventor: Oren Gavriely, 116A Moriah Avenue, Haifa (IL) 34618

( * ) Notice: Subject to any disclaimer, the term of this patent is extended or adjusted under 35 U.S.C. 154(b) by 424 days.

(21) Appl. No.: 10/534,402

(22) PCT Filed: Nov. 11, 2003

(86) PCT No.: PCT/IL03/00939

§ 371 (c)(1),
(2), (4) Date: May 10, 2005

(87) PCT Pub. No.: WO2004/043527

PCT Pub. Date: May 27, 2004

(65) Prior Publication Data

US 2006/0042630 A1    Mar. 2, 2006

(51) Int. Cl.
*A61M 11/00*  (2006.01)
(52) U.S. Cl. .......................... 128/207.14; 128/200.26; 128/207.29

(58) Field of Classification Search ............ 128/200.26, 128/207.14, 207.15, 207.29; 604/102.01, 604/103.01
See application file for complete search history.

(56) References Cited

U.S. PATENT DOCUMENTS

| | | | | |
|---|---|---|---|---|
| 3,707,151 A | * | 12/1972 | Jackson | 128/207.15 |
| 6,918,391 B1 | * | 7/2005 | Moore | 128/842 |
| 7,156,090 B2 | * | 1/2007 | Nomori | 128/200.26 |

* cited by examiner

*Primary Examiner*—Steven O Douglas

(57) ABSTRACT

A tube (30) for inducing gases into critically ill patients, in which the distal end (20) is perforated, and covered with an inflatable-deflatable sleeve (36). Gas is pumped into the proximal end of the tube (30), which inflates the sleeve (36) engaging the inner walls of an airway. The gas, typically a mixture of oxygen, subsequently exits the sleeve (36) and enters the airway. Auxiliary accessories (80) can be attached to the tube (30).

8 Claims, 7 Drawing Sheets

90

90

INTRA-AIRWAY VENTILATION

TECHNICAL FIELD OF THE INVENTION

The present invention deals generally with artificial ventilation of the critically ill. More specifically the invention is in the field of intra-tracheal ventilation devices.

BACKGROUND OF THE INVENTION

Artificial ventilation of critically ill, traumatized, or anesthetized persons is a life-saving procedure. Artificial ventilation may be performed by applying negative pressure around the chest with an "Iron Lung", or by pumping gas at positive pressure into the airways, called "Intermittent Positive Pressure Ventilation (IPPV)". IPPV may be applied through a tightly fitting face mask, or via a tube inserted into the trachea of the patient, called "Endotracheal Tube (ETT)". In recent years a hybrid method, namely the "laryngeal mask"—a catheter tip pear shape inflatable occluder that fits over the glottis at the entry to the trachea—has gained popularity. In addition to negative pressure ventilation and IPPV other (alternative) modes of ventilation have been described. These include "High Frequency Ventilation (HFV)", jet ventilation, "Constant Flow Ventilation (CFV)", and external chest vibration with tracheal bias flow.

To achieve effective IPPV, a tight seal must be formed between the gas delivery tube, such as the ETT or a tracheotomy tube, and the patient's airway. Thus, when gas (air; oxygen) pressure in the delivery tube rises it flows into, and only into, the person's lungs to induce inhalation. When the pressure in the gas delivery system falls bellow the pressure in the lungs the flow is reversed and $CO_2$-rich gas exits the lung. In conventional IPPV the expiratory outflow from the lung is through the same lumen of the ETT through which the gas flowed into the lung. Therefore, the lumen of the ETT must be as wide as possible to facilitate free exhalation without build-up of excessive intra-thoracic pressure.

When positive pressure ventilation is used, it is usually possible to control the respiratory rate, the volume of each breath (Tidal Volume) and the relative duration of the inspiratory and expiratory phases of each breath (I:E Ratio). It is also usually possible to control or limit the peak pressure during inspiration (PIP) and the minimal pressure at the end of expiration (PEEP). In addition, it is often desirable to facilitate self-triggering of the initiation of the breathing cycle by sensing the patient's brief drop in airway pressure induced by his/her inspiratory effort. This signal is used to actuate the delivery of a breath by the ventilator in tandem with the patient's own inspiratory effort.

While there are many models of ventilators with a variety of features and controls, all IPPV systems are only capable of ventilating the whole lung en bloc, or, at the most ventilating the two lungs with a special, two lumens ETT, using two ventilators. Current technology does not allow ventilation of lobes or segments of the lung individually, despite the substantial inhomogeneity of the disease processes encountered in most lung diseases.

German Patent 2055049 and U.S. Pat. No. 5,265,593 the contents of which are incorporated herein by reference, disclose an endotracheal tube equipped with a cuff balloon that is connected via an accessory channel to an actuating apparatus that rhythmically inflates the sleeve, while a steady flow of air or oxygen is blown through the main lumen of the tube. When the cuff baloon is inflated inside the patient's trachea it occludes the exit of air around the tube and the lungs inflates. When the cuff balloon is deflated, the lungs deflate with gas exiting around the tube, while gas is still flowing into the trachea through the tube's main channel. The lack of control over intra thoracic pressure leading to risk of lung hyperinflation and pneumothorax are major concerns with this method. The invention disclosed herewith describes an improved intra-tracheal ventilation method and tube that overcomes the deficiencies of the previous method.

DETAILED DESCRIPTION OF THE PRESENT INVENTION

Figure 1:
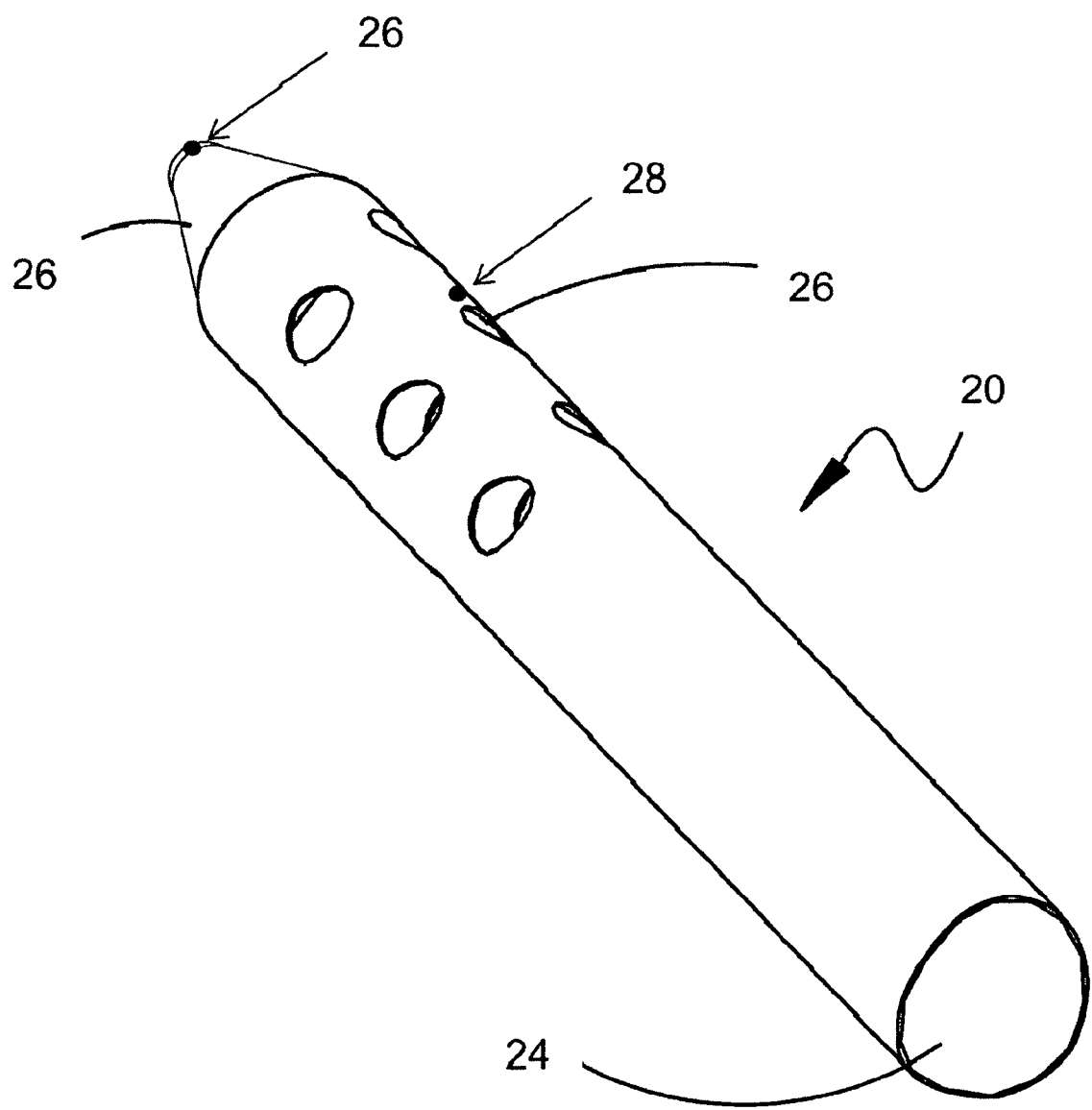
FIG. 1 is a schematic isometric description of a distal part of a tube of the invention.
Figure 2:
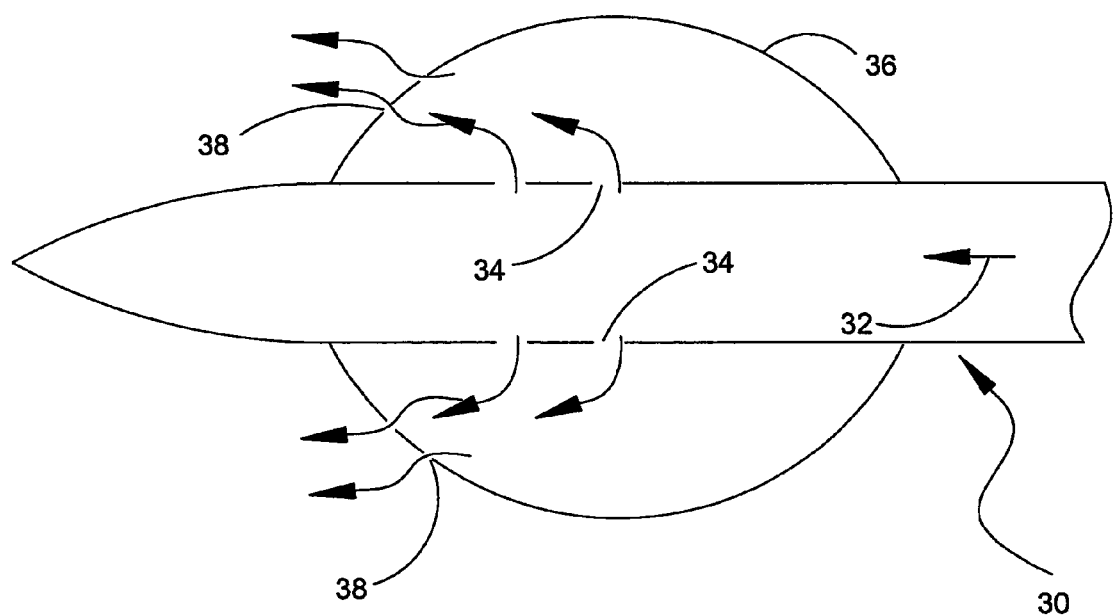
FIG. 2 is a schematic cross sectional view of a distal part of a tube of the invention in which the sleeve attached is inflated.
Figure 3A:
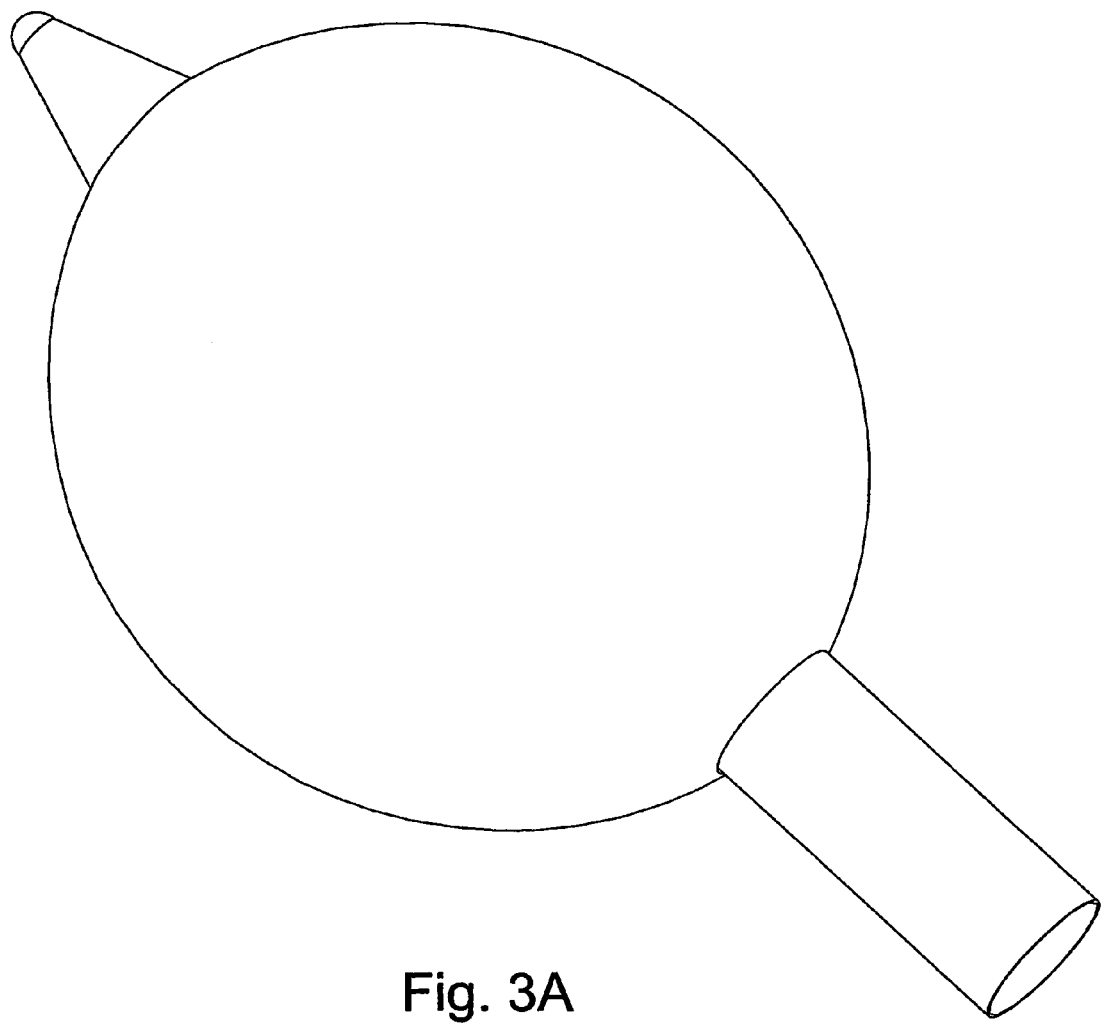
FIG. 3A is a schematic isometric view of a inflated sleeve over the distal side of a tube of the invention.
Figure 3B:
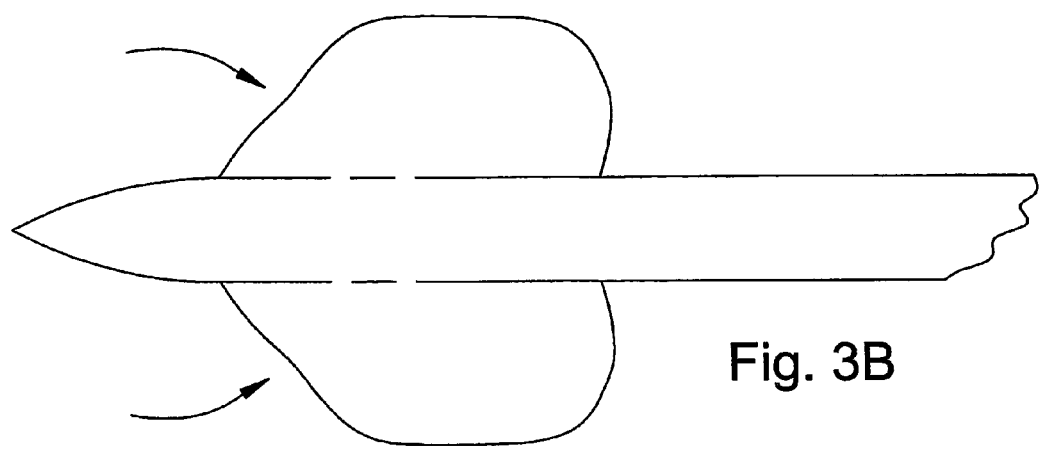
FIG. 3B is a schematic cross sectional view in a tube sleeve combination.
Figure 3C:
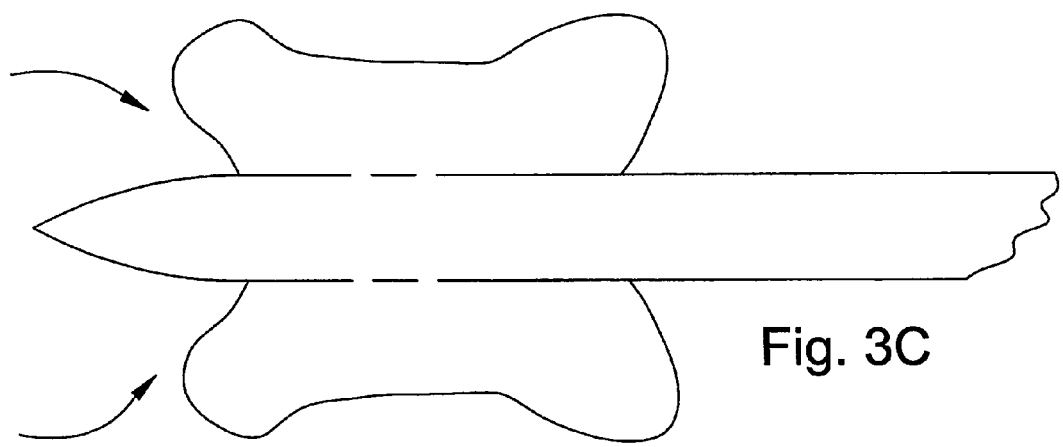
FIG. 3C is a schematic cross sectional view in a tube sleeve combination.
Figure 3D:
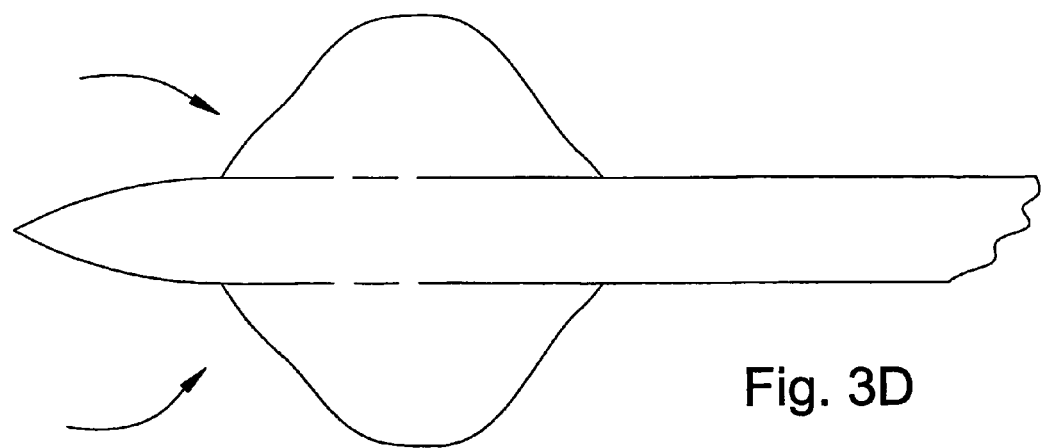
FIG. 3D is a schematic cross sectional view in a tube sleeve combination.

In accordance with the present invention, an intra-tracheal ventilation apparatus consists of a thin tube whose distal end is inserted into the patient's trachea. The distal end of the tube is surrounded by an inflatable/deflatable elastic sleeve (cuff balloon) whose inner volume is connected to the lumen of the tube via one or a plurality of perforations in the wall of the tube. In FIG. 1 to which reference is now made, A distal end 20 (the side inserted in the body) of a tube of the invention is shown isometrically. The tube is perorated with holes such as hole 22. The lumen 24 of the tube is shut off by tip 26 but the perforations facilitate a direct connection between the lumen and the external volume. The perforated zone is covered completely by an inflatable sleeve attached to the tube by an air-tight (hermetic) binding at both extremities zone. The proximal end of the tube is connected to an intermittent gas delivery system that blows pulses of compressed gas at a specified flow rate and frequency into the lumen of the tube. When gas such as air or an oxygen mixture is blown into the tube, sleeve first inflates and expands to a volume that is sufficient to occlude the airway in which it resides. This is better explained with reference to FIG. 2. Air or another combination of oxygen is pumped through the lumen of the tube 30 in the direction of arrow 32 to be subsequently excluded through perforations 34 into the lumen of the inflated sleeve 36, and from there to the ambient volume. In a typical case the ambient volume is the lumen of a tracheal element. The gas exits the sleeve through perforations such as perforations 38 in the distal side. In an inflated state the sleeve may take the form of a sphere as in FIG. 3A to which reference is now made, or other forms to better fit and subsequently block the inner surface of the airway. In FIGS. 3B-D cross sections in some other forms of sleeves are shown schematically in a inflated state. In FIG. 3B the sleeve is tapered at the front. In FIG. 3C the sleeve is constricted at the middle, and in FIG. 3D the sleeve is tapered at the front and back parts. In each case the arrows denote the general area in which the perforations are situated. The sleeve attached to the tube is extendable and retractable, facilitating reversible airtight locking of airways in the human or animal body. Variations in the sleeves are provided to accommodate for a variable number of perforations in the sleeve and the extent and form of blocking area abutting the inner walls of the airway. Thus different sleeves are provided, of different sizes (circumference and length) to best fit the airways of certain individuals. The sleeves are made by using specific mold forms, or by 5 incorporating a fine mesh of non-stretchable fibers at the desired shape in the balloon's wall material.

Figure 4:
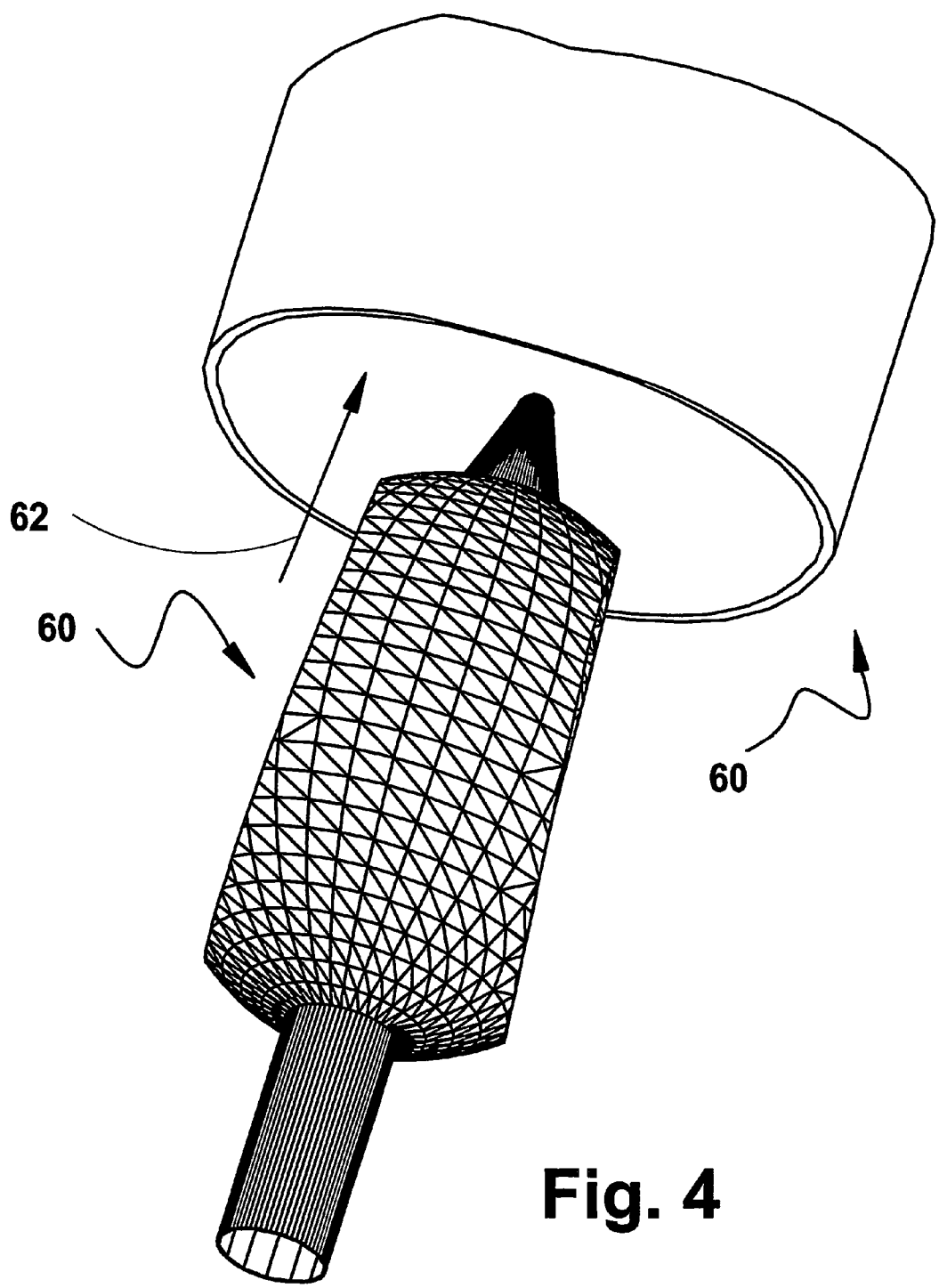
FIG. 4 is a schematic isometric view of a distal end of a sleeved tube inserted into an airway.

In FIG. 4 to which reference is now made, a schematic description of an insertion of a tube tip with deflated sleeve 60, which is pushed in the direction of arrow 62 towards the lumen of an airway 64.

As a functional example, the tip of the tube of the invention is introduced into an airway in the lung and as gas is blown into the tube, it exits through its perforations, filling the lumen of the sleeve. As the sleeve extends, it lock to the walls of the airway, permitting flow through the perforations in the front (distal side) of the sleeve. This gas can now inflate the lung or lung portions whose main airway is occluded by the inflated balloon. When gas pumping diminishes, at the end of each pulse, the pressure inside the tube's lumen immediately falls and the inflated sleeve deflates through the hole. As the sleeve deflates it loosens its grip on the internal walls of the blocked airway, allowing for exhaled gas to exit the lungs or lung portion. In accordance with preferred embodiment of the invention the deflation of the sleeve is induced by the elastic recoil of the sleeve, constructed from an elastomer thin membrane such as silicone that can expand and relax thousands of times without changing its elastic properties.

Alternatively, applying suction (negative pressure) to the tube collapses the sleeve or enhances the collapse.

In some embodiments, a portion of the distal tip of the tube is removed, to be replaced by a diffuser, allowing flow of some of the gas by passing the pores in the diffuser, whereas the rest of the flowing gas passes through the perforations in the walls of the tube and sleeve, respectively.

In yet another embodiment, the sleeve wall is not perforated tube is open, either directly or with a diffuser, allowing all the gas to flow into the while the tip of the lumen of the airway in which it is lodged after expanding the sleeve by passing a small amount of gas into the sleeve through the holes in the tube wall beneath the sleeve. In this embodiment, the sleeve deflates through the same connecting holes in the tube wall. This occurs when the pressure inside the tube drops at the end of the inspiratory gas delivery pulse.

Pressure Sensing

Adding a pressure-sensing element at the distal side of the tube to sense the intra-airway pressure throughout the ventilation may be advantageous. Reference is now made again to FIG. 1, in which pressure transducer 26 is shown. Such a pressure sensing may be achieved by a pressure transducer 26, which for instance can be the Milar® catheter-tip transducer or any other sensor known in the art suitable for such purpose, or by passing a narrow pressure-sensing catheter through the length of the tube with a forward directed opening (not shown). The information on the intra-airway pressure may be monitored continuously. The information on the pressure at any time during the ventilation may be used to prevent excessive intra-airway pressure build-up, beyond a pre-set value, such as 30 cm $H_2O$. The information about the pressure may also be used to determine and control the desired peak inspiratory pressure (PIP) during each breath and the desired positive end expiratory pressure (PEEP). The pressure tracking at the distal end of the tube may also be used to trigger a pulse of gas flow (a breath) when the level of pressure transiently drops due to the patient's own inspiratory effort. In addition to the pressure sensor, a gas composition sensor 28 may be employed as well, to alert of undesirable component or component ratio in the gas composition at the surrounding volume.

Accessories to the Tube

Figure 5:
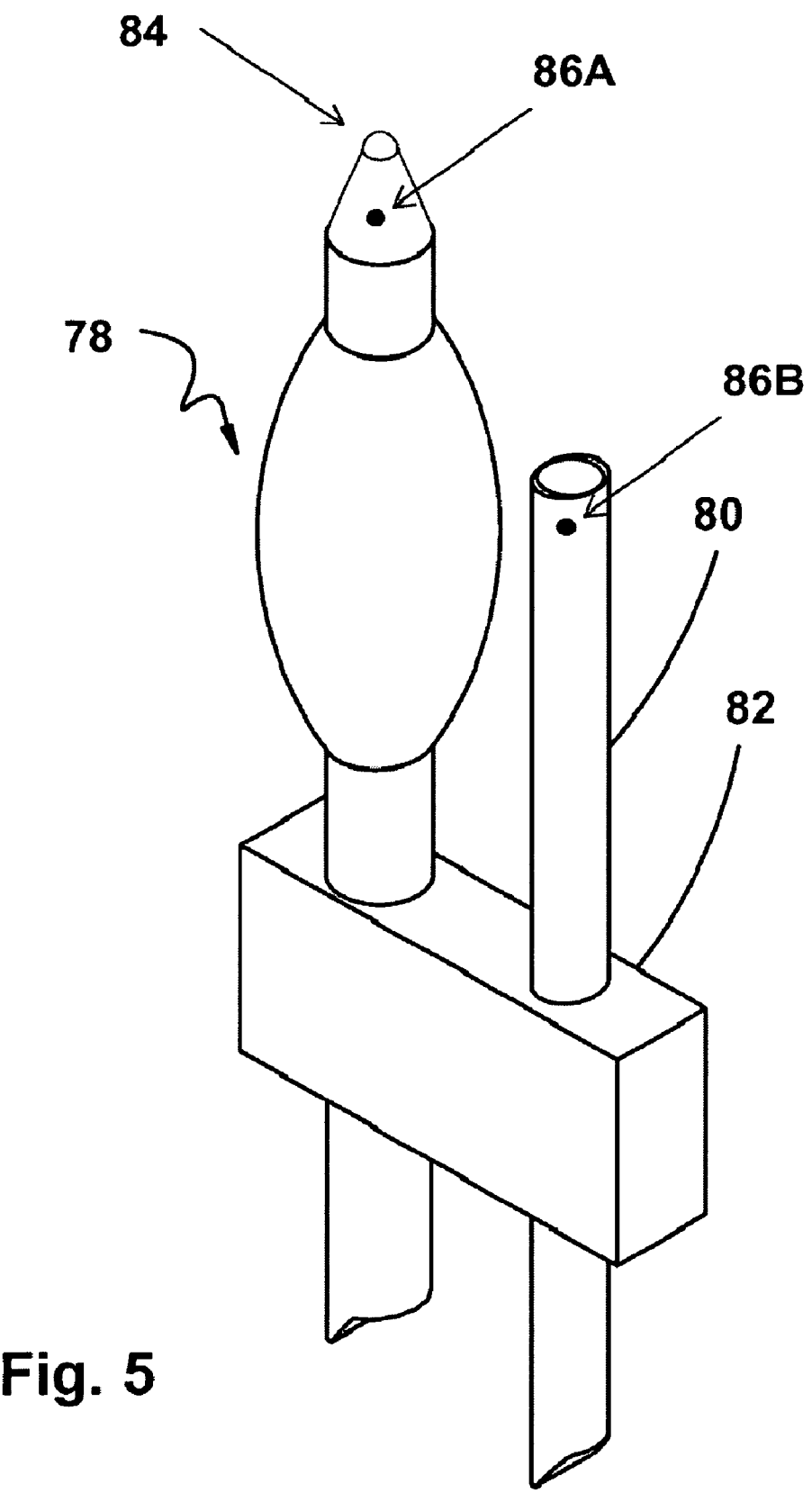
FIG. 5 is a schematic isometric view of an accessory tube in combination with the standard tube of the invention.

In FIG. 5 to which reference is now made shows a sleeve 78 and a tube of the invention, aligned and secured with an accessory tube 80, typically a catheter, in parallel by a clamp 82. The clasp may optionally allow a sliding movement of the accessory tube along the length of the clamp. This allows variable positioning of the orifice of the accessory tube with respect to the sleeve and tip. A secondary catheter or probe may be used to extract secretions from the airways by suction, lavage the lung, insert medications. Tubes or other cylindrical element may be use in the accessory position, in addition to catheters. Very useful examples are observation means for the airways using a fiber-optic scope or a miniature video camera 84, or obtaining samples of the airway tissue and lining by brushing or with a biopsy tool.

Another feature of the device of the invention is a proximal side-port with an appropriate connector such as a Luer lock with a one-way valve that allows injection of agents such as liquids or gases or aerosols into the gas stream flowing into the patient's airways. These liquids may contain medications, such as adrenaline or atropine.

Additional accessories at the tip of the tube or at the tip of an auxiliary tube may be a microphone 86A or 86B or a video camera, such as camera 84, which constitute optional gatherers of information for monitoring the welfare of the patient or the progress of insertion of the tube inside the patient.

Tube Stabilizing and Insertion Limiters

Figure 6A:
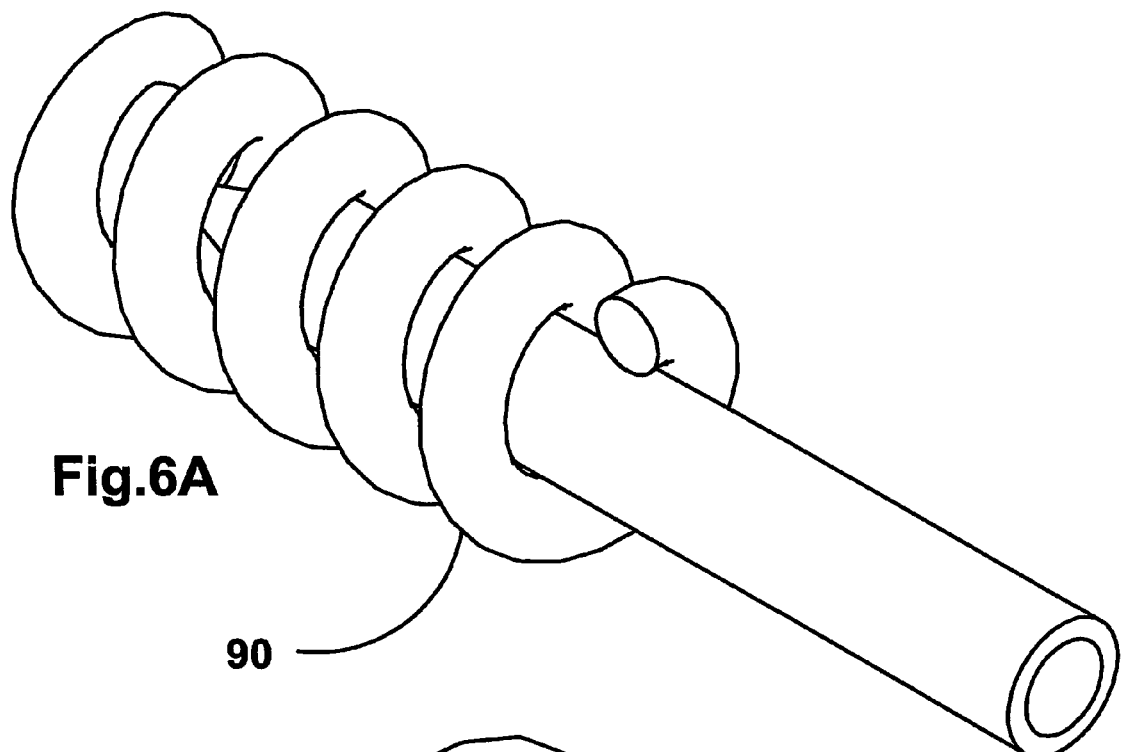
FIG. 6A is a schematic isometric view of a stabilizing spring at the distal side of the tube of the invention in a contracted position.
Figure 6B:
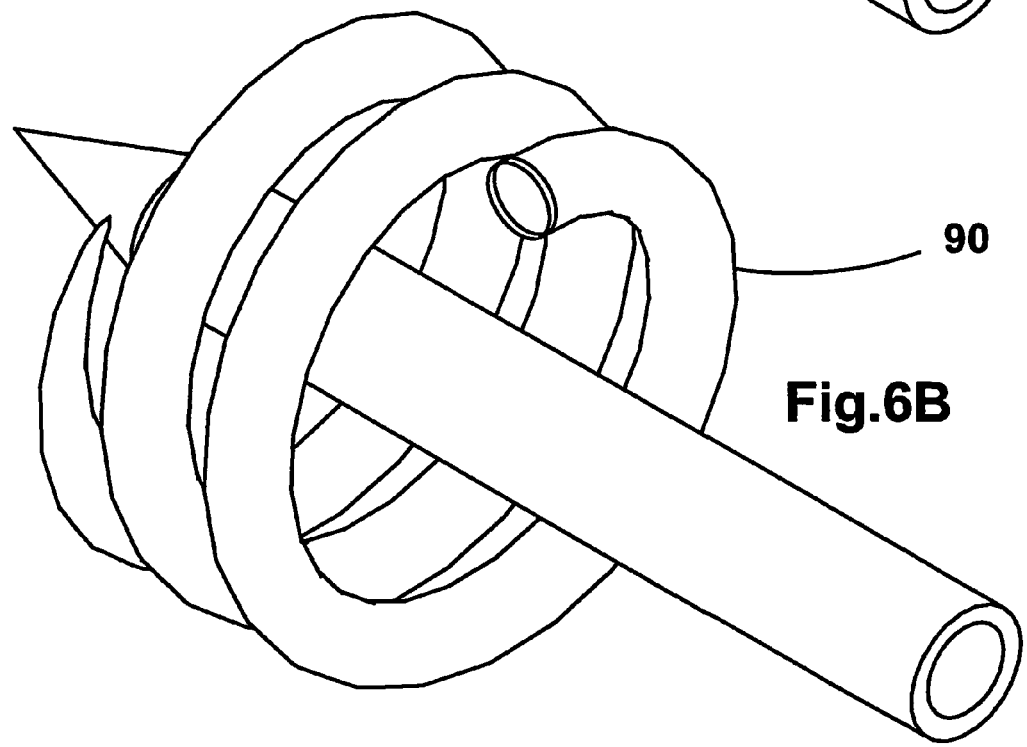
FIG. 6B is a schematic isometric view of a stabilizing spring at the distal side of the tube of the invention in a released position.

Additionally we disclose a method to prevent insertion of the tube too far into the airways, thereby avoiding the risk of wedging the tube in an airway. This is achieved by equipping the tip of the tube with a hinged ring of a diameter matching the narrowest airway in which the tip of tube is to be lodged. The ring prevents the catheter from being advanced too far into the lung. The ring may be made from a rigid material such as bio-compatible metal or plastics. Alternatively, the ring may be made from an inflatable narrow tube connected via a secondary channel to an external inflating device such as a syringe. Alternatively, as described schematically in FIGS. 6A-6B to which reference is now made, a contracted spring 90 as in FIG. 6A may be released as in FIG. 6B for adhering to the inner walls of the airway. The spring may be concealed by a retractable thin-wall sleeve during the insertion of the tube into the trachea. Once inside the trachea, the sheet may be retracted by pulling it back, allowing the pre-stressed coiled element to spring out and attain its unstressed shape and dimensions inside the airways. The same method be useful to stabilize the tip of the tube and keep it about the centre of the airway.

Special Uses of the Invention

Under certain circumstances it is important to selectively ventilate different lung regions. This is particularly desirable when the lung disease is highly non-homogenous. The device may be used for such application. This is achieved by inserting a plurality of tubes selectively into main-stem or lobar bronchi. These tubes are narrower and have smaller sleeves than the standard ones, but are otherwise similar in construction and function. The tubes may be positioned using a fiber-optic or video camera scope that can be maneuvered to specific sites in the airways. Additionally, certain lung regions may be inflated to higher pressures while others are kept at low inflation pressure. It is possible using the device of the invention to apply one or more intra-airway ventilation catheters by passing them through a standard tube for combined selective and global ventilation of the lung.

The invention claimed is:

1. A tube for introducing gases into critically ill patients comprising:
 a perforated zone at or near the distal end of said tube, and
 an inflatable/deflatable sleeve covering said perforated zone of said tube allowing direct connection between the lumen of said tube and the lumen of said sleeve, wherein said sleeve is hermetically bound peripherally at its two extremities to said tube, allowing flow of gas from the lumen of said tube to an airway in which the tube tip is inserted;
 wherein the distal orifice of said tube is sealed.

2. A tube for introducing gases into critically ill patients comprising:
 a perforated zone at or near the distal end of said tube, and
 an inflatable/deflatable sleeve covering said perforated zone of said tube allowing direct connection between the lumen of said tube and the lumen of said sleeve, wherein said sleeve is hermetically bound peripherally at its two extremities to said tube, allowing flow of gas from the lumen of said tube to an airway in which the tube tip is inserted;
 wherein a clamp holds said tube substantially in parallel with a cylindrical accessory.

3. A tube for inducing gases into critically ill patients as in claim 2 and wherein said cylindrical accessory is slidable with respect to said clamp.

4. A tube for introducing gases into critically ill patients comprising:
 a perforated zone at or near the distal end of said tube, and
 an inflatable/deflatable sleeve covering said perforated zone of said tube allowing direct connection between the lumen of said tube and the lumen of said sleeve, wherein said sleeve is hermetically bound peripherally at its two extremities to said tube, allowing flow of gas from the lumen of said tube to an airway in which the tube tip is inserted;
 wherein at least one sensor is disposed at substantially the distal end of said tube.

5. A tube for inducing gases into critically ill patients as in claim 4 and wherein said at least one sensor is a microphone.

6. A tube for inducing gases into critically ill patients as in claim 4 and wherein said at least one sensor is a camera.

7. A tube for inducing gases into critically ill patients as in claim 4 and wherein said at least one sensor is a pressure transducer.

8. A tube for inducing gases into critically ill patients as in claim 4 and wherein said at least one sensor is a gas composition sensor.

* * * * *